United States Patent [19]

Lunsford et al.

[11] 4,207,327
[45] Jun. 10, 1980

[54] N-(4-PYRAZOLIDINYL)BENZAMIDES AND THEIR AMINO PRECURSORS

[75] Inventors: Carl D. Lunsford, Richmond; Albert D. Cale, Jr., Mechanicsville, both of Va.

[73] Assignee: A. H. Robins Company, Inc., Richmond, Va.

[21] Appl. No.: 41,461

[22] Filed: May 22, 1979

Related U.S. Application Data

[63] Continuation-in-part of Ser. No. 930,125, Aug. 1, 1978, abandoned, which is a continuation-in-part of Ser. No. 900,369, Apr. 26, 1978, abandoned, which is a continuation-in-part of Ser. No. 826,031, Aug. 19, 1977, abandoned.

[51] Int. Cl.² .................. A61K 31/415; C07D 231/04
[52] U.S. Cl. .................................. 424/273 P; 548/356
[58] Field of Search ...................... 548/356; 424/273 P

[56] References Cited

U.S. PATENT DOCUMENTS

| | | | |
|---|---|---|---|
| 3,342,826 | 9/1967 | Miller et al. | 424/274 |
| 3,542,804 | 11/1970 | Daniels | 548/356 |
| 3,577,440 | 5/1971 | Lunsford et al. | 424/274 |
| 3,963,745 | 6/1976 | Cale, Jr. et al. | 260/326.83 |

FOREIGN PATENT DOCUMENTS 42-1284 of 1967 Japan.
367508 4/1963 Switzerland.

OTHER PUBLICATIONS

Iyengar et al., Chem. Abst., 1975, vol. 82, No. 30623r.

*Primary Examiner*—Alan L. Rotman
*Assistant Examiner*—Natalia Harkaway

[57] ABSTRACT

N-(4-Pyrazolidinyl)benzamides having the formula

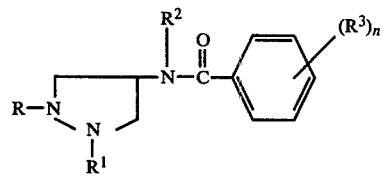

and their amino precursors are disclosed wherein R is lower alkyl, lower cycloalkyl or phenyllower-alkyl; $R^1$ is lower alkyl, lower cycloalkyl, or phenyllower-alkyl; $R^2$ is hydrogen, lower alkyl or phenyl; $R^3$ is hydroxy, cyano, nitro, amino, fluoro, chloro, bromo, trifluoromethyl, lower alkyl, lower alkoxy, sulfamoyl or actamido, $R^3$ can be the same radical or different radicals; n is an integer from zero to three inclusive, and pharmaceutically acceptable acid addition salts thereof. The compounds have anti-emetic and gastric emptying properties.

25 Claims, No Drawings

N-(4-PYRAZOLIDINYL)BENZAMIDES AND THEIR AMINO PRECURSORS

The present application is a continuation-in-part of copending application Ser. No. 930,125, filed Aug. 1, 1978, which was a continuation-in-part of then copending application Ser. No. 900,369, filed Apr. 26, 1978, now abandoned, which was a continuation-in-part of then copending application Ser. No. 826,031 filed Aug. 19, 1977, now abandoned.

BACKGROUND OF THE INVENTION

1. Field of Invention

The present invention is concerned with heterocyclic compounds possessing anti-emetic and gastric emptying properties and is particularly concerned with certain N-(4-pyrazolidinyl)benzamides, compositions thereof and methods for employing the compositions in controlling emesis and gastric emptying properties in warm blooded animals with minimal side effects.

2. Description of the Prior Art

The prior art discloses various benzamido derivatives wherein one of the substituents attached to the benzamido nitrogen can be a pyrrolidinyl or a piperidinyl radical. U.S. Pat. No. 3,342,826 discloses heterocyclic aminoalkyl benzamides having anti-emetic properties. U.S. Pat. No. 3,577,440 describes 1-substituted-3-amidopyrrolidines having analgetic and antidepressant properties. U.S. Pat. Nos. 3,966,957 and 3,963,745 describe N-(1-substituted-3-pyrrolidinyl) benzamides and thiobenzamides as particularly useful in controlling emesis.

SUMMARY OF THE INVENTION

The novel compounds of the present invention are N-(1,2-hydrocarbyl-4-pyrazolidinyl)benzamides (I). The novel compounds of the invention have the formula:

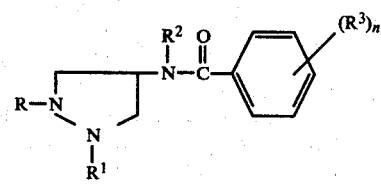

wherein;

R is lower alkyl, lower cycloalkyl or phenyllower alkyl, $R^1$ is lower alkyl, lower cycloalkyl or phenyllower alkyl, $R^2$ is hydrogen, lower alkyl or phenyl, $R^3$ is hydroxy, cyano, nitro, amino, fluoro, chloro, bromo, trifluoromethyl, lower alkyl, lower alkoxy, sulfamoyl or acetamido, $R^3$ can be the same radical or different radicals, and n is an integer from zero to three inclusive.

The non-toxic pharmaceutically acceptable acid addition salts of the basic compounds of Formula I are also included within the scope of this invention, since such salts can likewise be used as anti-emetics or gastric emptying compounds. Both organic and inorganic acids can be employed to form the pharmaceutically acceptable acid addition salts, illustrative acids being sulfuric, nitric, phosphoric, citric, acetic, lactic, tartaric, sulfamic, succinic, fumaric, maleic, hydrochloric, hydrobromic, benzoic, and the like. The salts are prepared by methods well known to the art.

The anti-emetic properties were determined using a modification of the methods of Chen and Enxor, J. Pharmac. Exp. Ther. 98, 245-250 (1950) and of Leonard et al., J. Pharmac. Exp. Ther. 154, 339-345 (1966).

The gastric emptying activity was determined using the following procedure. Female Sprague-Dawley rats weighing 117-221 g. were starved 24 hours in individual screen-bottom cages with water ad libitum. Animals were arranged in groups of eight. At time 0, 9 mg/kg of a test compound is administered intraperitoneally to the rats in 5% acacia (0.4 ml/100 g. body weight). The control group is dosed with acacia alone, 4 ml/kg intrapertioneally. Thirty minutes following dosing, the rats are given orally, by stomach tube, 3 ml. of a test meal consisting of methylcellulose base to which had been added beef bouillon, casein, powdered sugar and corn starch to yield a semi-solid homogenous paste. Sixty minutes following the test meal (ninety minutes total time), the rats are sacrificed by cervical dislocation, laparotomized and the stomachs removed. The full stomachs are weighed on an analytical balance after which they are cut open, rinsed and the empty stomach weighed. The difference between full and empty stomach weights represents the amount of meal remaining in the stomach and is subtracted from the weight of 3.0 ml. of test meal to yield the amount of meal emptied from the stomach during the test period.

The preferred compound of Example 6 reduced emesis 87% when administered at a dose level of 5 mg/kg (s.c.) and increased the gastric emptying time significantly when administered at doses from 0.33 to 9.0 mg/kg.

It is, therefore, a primary object of the present invention to provide N-(4-pyrazolidinyl)benzamides. A further object is to provide novel N-(4-pyrazolidinyl)benzamides having anti-emetic and gastric emptying properties. A still further object is to provide novel compositions useful as anti-emetics and for controlling gastric emptying.

Additional objects and advantages of the present invention will be apparent to one skilled in the art and still others will become apparent from the following description of the best mode of carrying out the present invention and from the appended claims.

The lower alkyl moiety has 1-4 carbon atoms.

The term "lower cycloalkyl" as used herein includes primarily cyclic alkyl radicals containing from four up to twelve carbon atoms inclusive and includes such groups as cyclobutyl, cyclopentyl, cyclohexyl, cycloheptyl, methylcyclopentyl, ethylcyclohexyl and the like.

The term "phenyl" as used herein includes the unsubstituted phenyl radical and phenyl radicals substituted by any radical or radicals which are not reactive or otherwise interfering under the conditions of reaction described herein such as lower-alkyl, lower-alkoxy, trifluoromethyl, bromo, chloro, fluoro, and the like. The substituted phenyl radicals have preferably no more than three substituents such as those given above and, furthermore, these substituents can be in various available positions of the phenyl nucleus and when more than one substituent is present, can be the same or different and can be in various position combinations relative to each other. The lower-alkyl and lower-alkoxy substituents each have preferably from one to four carbon atoms which can be arranged as straight or branched chains. Examples of the preferred substituents are methyl, ethyl, propyl, butyl, fluoro, bromo, chloro, iodo, amino, hydroxy, cyano, acetamido, sulfamoxyl, methoxy, ethoxy, propoxy, butoxy and trifluoromethyl radicals.

The term "lower-alkyl" includes straight and branched chain radicals containing 1 to 8 carbon atoms as, for example, methyl, ethyl, propyl, isopropyl, n-butyl, tertiary butyl, amyl, isoamyl, n-hexyl, n-heptyl, and n-octyl radicals. A "lower-alkoxy" radical has the formula -0-lower alkyl.

Included in the term "phenyllower-alkyl" are such groups as benzyl, phenethyl, phenpropyl, amethylbenzyl, and the like.

Also included within the scope of the present invention are novel 4-amino-1,2-hydrocarbylpyrazolidines (II). The compounds of Formula II have the formula:

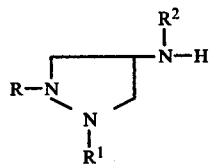

wherein R is lower alkyl, lower cycloalkyl or phenyl-lower alkyl; $R^1$ is lower alkyl, lower cycloalkyl or phenyllower alkyl; $R^2$ is hydrogen, lower alkyl or phenyl.

The compounds of Formula II wherein $R^2$ is hydrogen are prepared by heating a mixture of a 4-halo-1,2-hydrocarbylpyrazolidine and concentrated ammonium hydroxide in a steel bomb at a temperature of from about 125° C. to about 200° C. for a period of several hours. The procedure is also applicable to prepare compounds wherein $R^2$ is lower alkyl such as methyl, ethyl, or propyl. In the latter case a solution of the appropriate lower alkylamine in a lower alkanol is preferably used.

The compounds of Formula II wherein $R^2$ is phenyl are prepared by reacting a 1,2-hydrocarbyl-4-arylsulfonyloxy-pyrazolidine and aniline or a substituted aniline together in a suitable solvent. The 1,2-hydrocarbyl-4-arylsulfonyloxy-pyrazolidine is generally prepared by reacting the sodium salt of a 1,2-hydrocarbyl-4-pyrazolidinol with benzenesulfonyl chloride or p-tolylsulfonyl chloride in a dry aprotic solvent such as toluene.

The 1,2-hydrocarbyl-4-pyrazolidinols from which the respective 4-aminopyrazolidinols are prepared are either disclosed in or they can be prepared by the procedures disclosed in U.S. Pat. No. 3,660,426.

The novel basic compounds of Formulas I and II from fluosilicic acid addition salts which are useful as moth-proofing agents according to U.S. Pat. Nos. 1,915,334 and 2,075,359.

Method of Preparation

The preparation of the benzamido compounds of Formula I may be accomplished by contacting a 4-amino-1,2-hydrocarbylpyrazolidine II, with an appropriately substituted benzoyl chloride III according to the following reaction sequence:

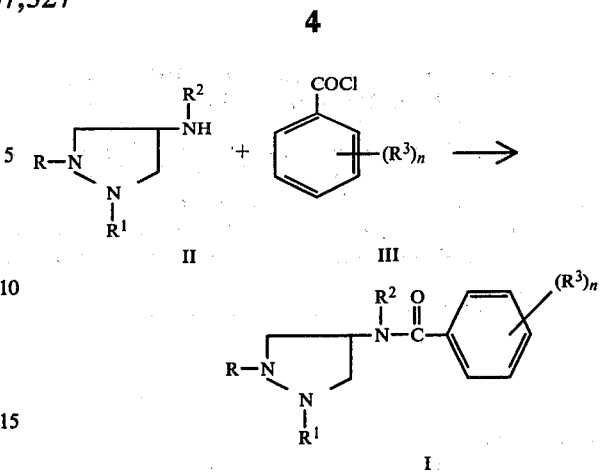

wherein R, $R^1$, $R^2$, and n are as defined above with the proviso that $R^3$ cannot be primary amino.

Compounds of Formula I wherein $R^3$ is primary amino are generally prepared by catalytic hydrogenation of the precursor compound of Formula I wherein $R^3$ is nitro. Alternately, a compound of Formula I is prepared having $R^3$ is an acetamido radical and the compound is hydrolyzed in dilute acid to generate the amino radical.

In an alternate method of preparation 1,2-hydrocarbyl-4-phthalimidopyrazolidines are used as a reactant. The latter are prepared by the reaction between a 4-chloro-1,2-hydrocarbylpyrazolidine and potassium phthalimide. The 1,2-hydrocarbyl-4-phthalimidopyrazolidine is hydrolyzed in dilute mineral acid, the mixture filtered and the acid filtrate basified to liberate the free 4-amino-1,2-hydrocarbylpyrazolidine which is reacted with a selected benzoyl chloride to give the desired N-(1,2-hydrocarbyl-4-pyrazolidinyl)-benzamide.

Another alternate method which can be used in preparing the novel compounds of Formula I utilizes an appropriately substituted benzoic acid which is contacted with ethylchlorocarbonate in the presence of triethylamine in methylene chloride at 0°–5° C. to form the mixed anhydride of the benzoic acid. After approximately one hour at the lower temperature, a solution of the 4-amino-1,2-hydrocarbylpyrazolidine is added. Subsequent to an additional period of stirring, an aqueous sodium bicarbonate solution is added to the reaction mixture, the organic phase is separated and the benzamide compound is isolated therefrom by suitable means.

The substituted benzoyl chlorides III useful in practicing the present invention are either known compounds or they can be prepared by procedures well known to the art and include but are not limited to the following:

2-fluorobenzoyl chloride
3-bromobenzoyl chloride
4-bromobenzoyl chloride
3,5-dinitrobenzoyl chloride
3,4-dichlorobenzoyl chloride
3,4-diethoxybenzoyl chloride
3-trifluoromethylbenzoyl chloride
4-tertiarybutylbenzoyl chloride
4-butoxybenzoyl chloride
2,4-dimethoxybenzoyl chloride
4-methylbenzoyl chloride
4-cyanobenzoyl chloride
2-methoxy-5-sulfamoylbenzoyl chloride 2-methoxy-4-dimethylaminobenzoyl chloride
2-methoxy-4-nitrobenzoyl chloride
2-methoxy-3-fluoro-5-chlorobenzyl chloride
2-ethoxy-4-bromobenzoyl chloride
2-methoxy-3-acetamido-5-trifluoromethylbenzoyl chloride In Formula I centers of asymmetry are present. The compounds can be resolved into their optically active forms by combining the compounds with optically active organic acids and separating the optically active forms by fractional crystallization. The optically active forms are included within the scope of the present invention.

Preparation 1

4-Chloro-1,2-diethylpyrazolidine.

A solution of triphenyl phosphine (52 g.; 0.2 mole) in 150 ml. of chloroform was treated with chlorine gas which was accompanied by a rise in the temperature of the mixture to 60° C. until excess chlorine gas appeared over the surface of the mixture. Air was passed into the mixture until the greenish yellow gas disappeared. To the cooled (30° C.) stirred mixture was added dropwise 28.8 g. (0.2 mole) of 1,2-diethyl-4-pyrazolidino at a rate which caused the reaction mixture to rise to 40° C. Subsequent to the addition, the stirred solution was refluxed two hours, cooled to room temperature and extracted with water. The combined aqueous extracts were basified with concentrated sodium hydroxide solution and the basic mixture extracted with chloroform. The dried chloroform extract (sodium sulfate) was concentrated at reduced pressure and the residual material distilled at 92°-94° C./30 mm. to give 24.5 g. (75%) of product.

Analysis: Calculated for $C_7H_{15}N_2Cl$: C,51.68; H,9.29; H,17.22; Found: C,51.45; H,9.30; H, 17.29.

Preparation 2

4-Amino-1,2-diethylpyrazolidine

A mixture of 100 g. (0.615 mole) of 4-chloro-1,2-diethylpyrazolidine and 200 ml. of concentrated ammonium hydroxide in a closed steel chamber was heated at 150° C. for approximately 36 hours. The cooled reaction mixture was extracted with isopropyl ether, the aqueous layer saturated with potassium carbonate and continuously extracted with chloroform for six hours. The dried chloroform extract (sodium sulfate) was concentrated at reduced pressure and the residue distilled at 113°-115° C./40 mm. to give 40.5 g. (45.5%) of product.

Preparation 3

4-Amino-1,2-dimethylpyrazolidine.

A mixture of 300 g. (2.22 mole) of 4-chloro-1,2-dimethylpyrazolidine and 600 ml. of conc. ammonium hydroxide was heated at 150° C. for 18 hours. in a steel bomb. The cooled mixture was saturated with potassium carbonate and continuously extracted for 18 hrs. with chloroform. The residual material after concentration of the chloroform extract was distilled at 90°-100° C./40 mm. to give 73 g. of product.

Preparation 4

4-Anilino-1,2-dimethylpyrazolidine.

A stirred suspension of 40 g. (1.02 mole) of sodamide in dry toluene was treated dropwise with 116 g. (1.0 mole) of 1,2-dimethyl-4-pyrazolidinol at 80° C. After 4.5 hrs. at reflux the mixture was cooled and maintained below 20° C. while 161.0 g. (1.0 mole) of benzenesulfonyl chloride was added dropwise. After stirring 1.0 hr. the reaction mixture was shaken with dilute sodium hydroxide, the separated toluene layer dried over sodium sulfate and concentrated at reduced pressure. The residue was dissolved in 300 ml. of aniline, the mixture heated 2.5 hrs. on the steam bath and refluxed for 3.0 hrs. The cooled mixture was extracted with dilute sodium hydroxide solution and the separated aqueous layer extracted with isopropyl ether. The combined organic layers after drying over sodium sulfate were concentrated and the residue distilled to a pot temperature of 140° C./80 mm. The residue which would not crystallize was distilled at 110°-125° C./0.1 mm. to give 86 g. of product.

Preparation 5

4-Anilino-1,2-diethylpyrazolidine.

To a stirred suspension of 7.9 g. (0.2 mole) of sodamide in 100 ml. of dry toluene was added 28.8 g. (0.2 mole) of 1,2-diethyl-4-pyrazolidinol at a rate so that a pot temperature of 30°-35° C. was maintained. After stirring 2.0 hrs. at room temperature, the solution was added dropwise to a solution of 38.0 g. (0.2 mole) of p-toluenesulfonyl chloride in 200 ml. of dry toluene with the pot temperature maintained below 30° C. After stirring for about one hr. at room temperature, the reaction mixture was washed twice with water and dried over sodium sulfate. The dried filtered solution was concentrated to a volume of about 100 ml., aniline (100 ml.) was added, the solution refluxed for 3.0 hrs. and then concentrated. The residue was partitioned between chloroform and dilute sodium hydroxide. The dried chloroform layer was concentrated and the residue distilled at 120° C./0.1 mm. to give 4.0 g. of product.

Preparation 6

1,2-Diethyl-4-phthalimido-pyrazolidine Maleate.

To 100 ml. of dimethyl sulfoxide was added 32.4 g. (0.2 mole) of 4-chloro-1,2-diethylpyrazolidine and 37 g. (0.2 mole) of potassium phthalimide. The solution was stirred at 115° C. for 48 hours., cooled and filtered. The filtrate was treated with an equal volume of water and extracted 2 times with 150 ml. of ethyl acetate. The extracts were combined and concentrated. The residue was partitioned between dilute hydrochloric acid and ethyl acetate. The acid layer was made basic with potassium carbonate and extracted with chloroform. The chloroform was dried (sodium sulfate) and concentrated. The residue (22 g.) was treated with 22 g. of maleic acid and 75 ml. of isopropyl alcohol and 75 ml. of isopropyl ether. The maleate salt was recrystallized twice from the same solvent system to give 11.5 g. (15%) of product which melted at 144°-147° C.

Analysis: Calculated for $C_{19}H_{23}N_3O_6$: C,58.60; H,5.95; N,10.79; Found: C,58.64; H,6.03; n,10.73.

Preparation 7

4-Amino-1-benzyl-2-methylpyrazolidine.

4-Amino-1-benzyl-2-methylpyrazolidine, b.p. 115°-125° C./1.0 mm., was prepared from 1-benzyl-2-methyl-4-pyrazolidinol according to preparations 1 and 2.

Preparation 8

4-Amino-1-cyclohexyl-2-methylpyrazolidine Fumarate.

4-Amino-1-cyclohexyl-2-methylpyrazolidine, b.p. 90°–100° C./0.5 mm., was prepared from 1-cyclohexyl-2-methylpyrazolidinol according to preparations 1 and 2. The fumarate salt melted at 149°–151° C.

Preparation 9

4-Amino-1-isopropyl-2-methylpyrazolidine.

4-Amino-1-isopropyl-2-methylpyrazolidine, b.p. 110°–115° C./50 mm., was prepared from 1-isopropyl-2-methylpyrazolidinol according to preparations 1 and 2.

Preparation 10

When in the procedure of Preparation 2, concentrated ammonium hydroxide is replaced by an equal molar amount of methylamine in methanol, there is obtained 4-methylamino-1,2-diethylpyrazolidine.

EXAMPLE 1

4-Chloro-N-phenyl-N-(1,2-dimethyl-4-pyrazolidinyl)-benzamide.

To a solution of 10 g. (0.0525 mole) of 1,2-dimethyl-4-anilinopyrazolidine in 50 ml. of chloroform was added with stirring 9.15 g. (0.0525 mole) of p-chlorobenzoyl chloride with the temperature not exceeding 50° C. On completion of addition the solution was refluxed for one hour, cooled to room temperature and extracted with dilute sodium hydroxide. The chloroform layer was dried over sodium sulfate and concentrated at reduced pressure to give an oil which crystallized upon cooling. The solid was recrystallized twice from ligroin. Yield 13.1 g. (76%); m.p. 104°–108° C.

Analysis: Calculated for $C_{18}H_{20}ClN_3O$: C,65.54; H,6.11; N,12.74; Found: C,65.77; H,6.08; N,12.86.

EXAMPLE 2

4-Fluoro-N-(1,2-diethyl-4-pyrazolidinyl)benzamide.

A solution of 10 g. (0.026 mole) of 1,2-diethyl-4-phthalimidopyrazolidine maleate in 25 ml. of 6 N hydrochloric acid was refluxed two hours, the resulting mixture was cooled and filtered. The filter cake was washed with water which was combined with the acidic solution. The acidic solution was made basic with dilute sodium hydroxide and cooled with ice. To the resulting solution was added 8.2 g. (0.052 mole) of p-fluorobenzoyl chloride and the mixture shaken for 10 minutes. The resulting mixture was extracted with chloroform, the chloroform diluted with an equal volume of isopropyl ether and the resulting solution extracted with dilute hydrochloric acid. The acid layer was made basic with dilute sodium hydroxide and extracted with chloroform. The chloroform was dried (sodium sulfate) and concentrated. The residue was crystallized from isooctaneisopropyl ether and recrystallized from isooctaneisopropyl ether containing a few drops of ethyl acetate and clarified by charcoal treatment. The product (2.0 g; 29%) melted at 114°–116° C.

Analysis: Calculated for $C_{14}H_{20}N_3OF$: C,63.38; H,7.60; N,15.84; Found: C,63.36; H,7.61; N,15.96.

EXAMPLE 3

3,4,5-Trimethoxy-N-(1,2-dimethyl-4-pyrazolidinyl)benzamide.

To 10 g (0.09 mole) of 4-amino-1,2-dimethylpyrazolidine in chloroform was added with stirring 20.7 g. (0.09 mole) of 3,4,5-trimethoxybenzoyl chloride. After 30 minutes of stirring the solution was extracted with dilute sodium hydroxide. The chloroform solution was dried (sodium sulfate), filtered, and the filtrate concentrated. The resulting crystalline material was recrystallized from equal portions of ethyl acetate and isopropyl ether. The product (12.1 g.; 44%) melted at 163°–166° C.

Analysis: Calculated for $C_{15}H_{23}N_3O_4$: C,58.24; H,7.49; N,13.58; Found: C,58.20; H,7.45; N,13.19.

EXAMPLE 4

4-Nitro-N-(1,2-diethyl-4-pyrazolidinyl)benzamide Hydrochloride.

To a solution of 40.5 g (0.28 mole) of 4-amino-1,2-diethylpyrazolidine in 200 ml of chloroform was added with stirring 52 g (0.28 mole) of p-nitrobenzoyl chloride in 200 ml chloroform. The solution was allowed to stand overnight and then extracted with dilute sodium hydroxide. The chloroform was dried (sodium sulfate) and concentrated. The residue was crystallized twice from isopropyl etherethyl acetate to give 73 g. (80%) of the free base.

Analysis: Calculated for $C_{14}H_{20}N_4O_3$: C,57.52; H,6.90; N,19.17; Found: C,57.56; H,6.94; N,18.99.

The base was converted to the hydrochloride salt and crystallized from isopropyl alcohol which melted at 189°–191° C. (dec.).

Analysis: Calculated for $C_{14}H_{21}N_4O_3Cl$: C,51.14; H,6.44; N,17.04; Found: C,50.96; H,6.59; N,16.58.

EXAMPLE 5

4-Amino-N-(1,2-diethyl-4-pyrazolidinyl)benzamide.

A solution of 20 g. (0.069 mole) of 4-nitro-N-(1,2-diethyl-4-pyrazolidinyl)benzamide in ethanol was treated with Raney nickel and shaken in three atmospheres of hydrogen in a Parr apparatus at room temperature for two hours. The mixtures was filtered, the filtrate concentrated and the residue crystallized from isopropyl ether-ethyl acetate. The product (12.0 g.; 66.5%) melted at 119°–121° C.

Analysis: Calculated for $C_{14}H_{22}N_4O$: C,64.09; H,8.45; N,21.36; Found: C,63.98; H,8.55; N,21.37.

EXAMPLE 6

4-Amino-5-chloro-2-methoxy-N-(1,2-diethyl-4-pyrazolidinyl)benzamide.

To 75 ml. of thionyl chloride was added 12 g. (0.05 mole) of 4-acetamido-5-chloro 2-methoxy-benzoic acid and the stirred suspension refluxed one hour. The resulting solution was concentrated and 100 ml. of chloroform added to the residue which was concentrated to remove traces of thionyl chloride. The residue was dissolved in 100 ml. of chloroform and the solution added at a rapid drop to 7 g. (0.05 mole) of 4-amino-1,2-diethylpyrazolidine in 100 ml. of chloroform while stirring and cooling to 20°–25° C. with an ice bath. After 30 minutes the chloroform solution was extracted two times with 100 ml. of 3 N hydrochloric acid and the chloroform solution retained. The acid extract was boiled 10 minutes, cooled with ice, made basic with concentrated sodium hydroxide while cooling and extracted with chloroform. The chloroform was dried (sodium sulfate), concentrated and the residue crystallized from isopropyl ether-isooctane to give 3 g. of material which melted at 116°–118° C. The retained chloroform solution was extracted with dilute sodium hydroxide and concentrated. The residue was dissolved in 3 N hydrochloric acid and extracted with isopropyl ether. The acid solution was refluxed for 10 minutes, cooled with ice bath, made basic with sodium hydroxide while cooling and extracted with chloroform. The chloroform was dried (sodium sulfate) and concentrated. The residue was crystallized three times from isopropyl ether to give 0.7 g. of material which melted at 117°–119° C. A mixture melting point of both materials gave no depression of the melting point. The combined yield was 3.7 g. (23%).

Analysis: Calculated for $C_{15}H_{23}ClN_4O_2$: C,55.13; H,7.09; N,17.14; Found: C,55.23; H,7.10; N,17.17.

EXAMPLE 7

When in the procedure of Example 3 there is substituted for 3,4,5-trimethoxybenzoyl chloride equal molar amounts of:
  4-cyanobenzoyl chloride,
  3-trifluoromethylbenzoyl chloride,
  4-methylbenzoyl chloride,
  4-methoxybenzoyl chloride,
  4-acetamidobenzoyl chloride, and
  2-methoxy-5-sulfamoylbenzoyl chloride,
there are obtained:
  4-cyano-N-(1,2-dimethyl-4-pyrazolidinyl)benzamide,
  3-trifluoromethyl-N-(1,2-dimethyl-4-pyrazolidinyl)-benzamide,
  4-methyl-N-(1,2-dimethyl-4-pyrazolidinyl)benzamide,
  4-methoxy-N-(1,2-dimethyl-4-pyrazolidinyl)benzamide,
  4-acetamido-N-(1,2-dimethyl-4-pyrazolidinyl)-benzamide, and
  2-methoxy-5-sulfamoyl-N-(1,2-dimethyl-4-pyrazolidinyl)benzamide.

EXAMPLE 8

4-Amino-5-chloro-2-methoxy-N-(1,2-dimethyl-4-pyrazolidinyl)benzamide.

A stirred solution of equal molar amounts of 4-amino-5-chloro-2-methoxybenzoic acid and triethylamine in methylene chloride (0°–5° C.) was treated dropwise with a slight excess of ethylchlorocarbonate. After 1.0 hour a solution of 4-amino-1,2-dimethylpyrazolidine in methylene chloride was added and the mixture stirred for about two hours at room temperature. An aqueous solution of sodium bicarbonate was added to the reaction mixture, the organic phase separated and concentrated to give the product which melted at 169°–171° C.

EXAMPLE 9

4-Amino-5-chloro-2-methoxy-N-(1-benzyl)-2-methyl-4-pyrazolidinyl)benzamide Fumarate.

4-Amino-5-chloro-2-methoxy-N-(1-benzyl-2-methyl-4-pyrazolidinyl)benzamide was prepared from 4-amino-5-chloro-2-methoxybenzoic acid and 4-amino-1-benzyl-2-methyl-pyrazolidine according to the procedure of Example 8. The fumarate salt was prepared and it melted at 129°–131° C.

EXAMPLE 10

4-Amino-5-chloro-2-methoxy-N-(1-cyclohexyl-2-methyl-4-pyrazolidinyl)benzamide was prepared from 4-amino-5-chloro-2-methoxybenzoic acid and 4-amino-1-cyclohexyl-2-methylpyrazolidine according to the procedure of Example 8. Melting point of the hydrochloride hydrate was 105°–120° C.

EXAMPLE 11

4-Amino-5-chloro-2-methoxy-N-(1-isopropyl-2-methyl-4-pyrazolidinyl)benzamide Dihydrochloride.

4-Amino-5-chloro-2-methoxy-N-(1-isopropyl-2-methyl-4-pyrazolidinyl)benzamide was prepared from 4-amino-5-chloro-2-methoxybenzoic acid and 4-amino-1-isopropyl-2-methylpyrazolidine according to the procedure of Example 8. The dihydrochloride salt was prepared and it melted at 182°–186° C.

EXAMPLE 12

4-Amino-5-chloro-2-methoxy-N-(1,2-diethyl-4-pyrazolidinyl)benzamide Dihydrochloride.

To an ice-sodium chloride chilled stirring suspension of 46.34 g. (0.23 mole) of 4-amino-5-chloro-2-methoxybenzoic acid in 400 ml. of methylene chloride was added 23.23 g. (0.23 mole) of triethylamine. After the temperature had fallen to 0° C., 24.96 g. (0.23 mole) of ethyl chloroformate was added dropwise while maintaining a temperature of 0°–5° C. by ice bath cooling. The mixture was stirred at this temperature for 1 hour. To this was added dropwise at 0°–5° C. a solution of 32.26 g. (0.23 mole) of 1,2-diethyl-4-pyrazolidinamine in methylene chloride and stirring was continued for 0.5 hour at this temperature. The resulting mixture was washed with a dilute solution of sodium bicarbonate and the methylene chloride dried (sodium sulfate), filtered, and concentrated in vacuo. The residue was dissolved in 2-propanol, filtered, and made acidic to litmus by bubbling hydrogen chloride gas through the solution. The product was recrystallized from a mixture of ethanol, 2-propanol and isopropyl ether. A yield of 34.6 g. of product which melted at 182°–185° C. was obtained. To the filtrate was added additional isopropyl ether and after chilling, 15.35 g. of product which melted at 179°–185° C. was obtained. The combined yield was 49.95 g. (50%).

Analysis: Calculated for $C_{15}H_{25}N_4O_2Cl_3$: C,45.07; H,6.30; N,14.02; Found: C,45.24; H,6.21; N,14.08.

The pharmaceutical compositions of this invention comprise compounds of Formula I above in an amount to provide effective anti-emetic and gastric emptying action. The compositions contain 1.0 mg. to 100 mg. active medicament per unit dose. Preferably, the compositions contain from about 5 mg. to 100 mg. of medicament, advantageously from about 5 mg. to about 50 mg. per unit dose.

The pharmaceutical carrier employed in the composition can be either solid or liquid. Exemplary of solid carriers are lactose, magnesium stearate, terra alba, sucrose, talc, stearic acid, gelatin, agar, pectin or acacia. Exemplary of liquid carriers are vegetable oils and water. Similarly, the carrier or diluent may include a sustained release material such as glyceryl monostearate or glyceryl distearate alone or with a wax.

A wide variety of pharmaceutical forms can be employed by methods well known to the art. Thus, if a solid carrier is used the composition can be tableted or prepared as a powder, a troche or a lozenge. Gelatin capsules containing the medicament can also be prepared. If a liquid carrier is used, the composition can be in the form of a soft gelatin capsule, a liquid suspension or a syrup. Parenteral dosage forms are obtained by dissolving a water-soluble salt of the active agent in water or saline solution in a concentration such that 1 cc. of the solution contains from 1.0 mg. to 25 mg. of active agent. The solution can be filled into single or multiple dose ampules.

The method in accordance with this invention comprises administering internally to warm blooded animals including human beings certain N-(4-pyrazolidinyl)benzamides or a non-toxic organic or inorganic acid addition salt thereof, preferably with a non-toxic pharmaceutical carrier such as described above, in an amount sufficient to control emesis and/or facilitate gastric emptying. The active agent is administered orally or parenterally in repeated doses until satisfactory response is obtained. The daily dosage is from about 10 mg. to about 300 mg. of active medicament, advantageously from about 5 mg. to 50 mg.

What is claimed is:

1. A compound selected from the group consisting of N-(4-pyrazolidinyl)benzamides having the formula:

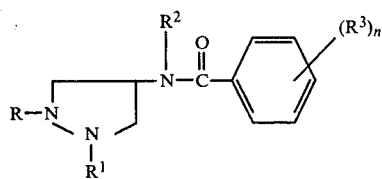

wherein;

R is lower alkyl, lower cycloalkyl or phenyllower alkyl, $R^1$ is lower alkyl, lower cycloalkyl or phenyllower alkyl, $R^2$ is hydrogen, lower alkyl or phenyl, $R^3$ is hydroxy, cyano, nitro, amino, fluoro, chloro, bromo, trifluoromethyl, lower alkyl, lower alkoxy, sulfamoyl or acetamido and $R^3$ can be the same radical or different radicals, and n is an integer from zero to three inclusive, and pharmaceutically acceptable acid addition salts thereof.

2. The compound of claim 1 which is 4-amino-5-chloro-2-methoxy-N-(1,2-dimethyl-4-pyrazolidinyl)-benzamide.

3. The compound of claim 1 which is 4-amino-5-chloro-2-methoxy-N-(1-benzyl-2-methyl-4-pyrazolidinyl)benzamide fumarate.

4. The compound of claim 1 which is 4-amino-5-chloro-2-methoxy-N-(1,2-diethyl-4-pyrazolidinyl)benzamide.

5. The compound of claim 1 which is 4-amino-5-chloro-2-methoxy-N-(1-isopropyl-2-methyl-4-pyrazolidinyl)benzamide dihydrochloride.

6. The compound of claim 1 which is 4-amino-5-chloro-2-methoxy-N-(1,2-diethyl-4-pyrazolidinyl)benzamide dihydrochloride.

7. A compound selected from 4-aminopyrazolidines having the formula:

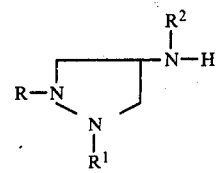

wherein:

R is lower alkyl, lower cycloalkyl or phenyllower alkyl, $R^1$ is lower alkyl, lower cycloalkyl or phenyllower alkyl, and $R^2$ is hydrogen, lower alkyl or phenyl.

8. A pharmaceutical composition useful for its antiemetic and gastric emptying properties, comprising (a) an emetic inhibiting and gastric emptying effective amount of a compound selected from the group consisting of N-(4-pyrazolidinyl)benzamides of the formula:

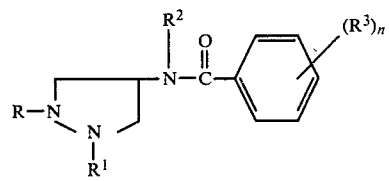

wherein;

R is lower alkyl, lower cycloalkyl or phenyllower alkyl, $R^1$ is lower alkyl, lower cycloalkyl or phenyllower alkyl, $R^2$ is hydrogen, lower alkyl or phenyl, $R^3$ is hydroxy, cyano, nitro, amino, fluoro, chloro, bromo, trifluoromethyl, lower alkyl, lower alkoxy, sulfamoyl or acetamido and $R^3$ can be the same radical or different radicals, and n is an integer from zero to three inclusive, and pharmaceutically acceptable acid addition salts thereof, and (b) a pharmaceutically acceptable carrier therefor.

9. A composition according to claim 8 wherein the active ingredient is 4-amino-5-chloro-2-methoxy-N-(1,2-dimethyl-4-pyrazolidinyl)benzamide.

10. A composition according to claim 8 wherein the active ingredient is 4-amino-5-chloro-2-methoxy-N-(1-benzyl-2-methyl-4-pyrazolidinyl)benzamide fumarate.

11. A composition according to claim 8 wherein the active ingredient is 4-amino-5-chloro-2-methoxy-N-(1,2-diethyl-4-pyrazolidinyl)benzamide.

12. A composition according to claim 8 wherein the active ingredient is 4-amino-5-chloro-2-methoxy-N-(1-isopropyl-2-methyl-4-pyrazolidinyl)benzamide dihydrochloride.

13. A composition according to claim 8 wherein the active ingredient is 4-amino-5-chloro-2-methoxy-N-(1,2-diethyl-4-pyrazolidinyl)benzamide dihydrochloride.

14. A method for treating warm blooded animals for emesis which comprises internally administering thereto an emesisinhibiting effective amount of a compound selected from the group consisting of N-(4-pyrazolidinyl)benzamides of the formula:

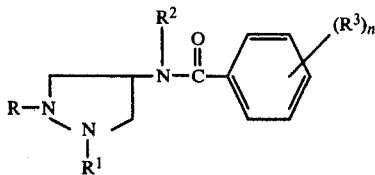

wherein;
- R is lower alkyl, lower cycloalkyl or phenyllower alkyl,
- $R^1$ is lower alkyl, lower cycloalkyl or phenyllower alkyl,
- $R^2$ is hydrogen, lower alkyl or phenyl,
- $R^3$ is hydroxy, cyano, nitro, amino, fluoro, chloro, bromo, trifluoromethyl, lower alkyl, lower alkoxy, sulfamoyl or acetamido and $R^3$ can be the same radical or different radicals, and
- n is an integer from zero to three inclusive, and pharmaceutically acceptable acid addition salts thereof.

15. The method of claim 14 wherein the compound is 4-amino-5-chloro-2-methoxy-N-(1,2-dimethyl-4-pyrazolidinyl)benzamide.

16. The method of claim 14 wherein the compound is 4-amino-5-chloro-2-methoxy-N-(1-benzyl-2-methyl-4-pyrazolidinyl)benzamide fumarate.

17. The method of claim 14 wherein the compound is 4-amino-5-chloro-2-methoxy-N-(1,2-diethyl-4-pyrazolidinyl)benzamide.

18. The method of claim 14 wherein the compound is 4-amino-5-chloro-2-methoxy-N-(1-isopropyl-2-methyl-4-pyrazolidinyl)benzamide dihydrochloride.

19. The method of claim 14 wherein the compound is 4-amino-5-chloro-2-methoxy-N-(1,2-diethyl-4-pyrazolidinyl)benzamide dihydrochloride.

20. A method of facilitating the gastric emptying in warm blooded animals which comprises internally administering thereto a gastric emptying effective amount of a compound selected from the group consisting of N-(1,2-hydrocarbyl-4-pyrazolidinyl)benzamides of the formula:

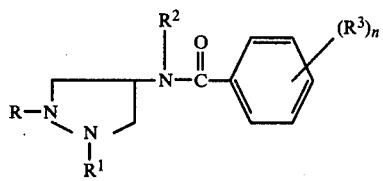

wherein;
- R is lower alkyl, lower cycloalkyl or phenyllower alkyl,
- $R^1$ is lower alkyl, lower cycloalkyl or phenyllower alkyl,
- $R^2$ is hydrogen, lower alkyl or phenyl,
- $R^3$ is hydroxy, cyano, nitro, amino, fluoro, chloro, bromo, trifluoromethyl, lower alkyl, lower alkoxy, sulfamoyl or acetamido and $R^3$ can be the same radical or different radicals, and
- n is an integer from zero to three inclusive, and pharmaceutically acceptable acid addition salts thereof.

21. The method of claim 20 wherein the compound is 4-amino-5-chloro-2-methoxy-N-(1,2-dimethyl-4-pyrazolidinyl)benzamide.

22. The method of claim 20 wherein the compound is 4-amino-5-chloro-2-methoxy-N-(1-bnezyl-2-methyl-4-pyrazolidinyl)benzamide fumarate.

23. The method of claim 20 wherein the compound is 4-amino-5-chloro-2-methoxy-N-(1,2-diethyl-4-pyrazolidinyl)benzamide.

24. The method of claim 20 wherein the compound is 4-amino-5-chloro-2-methoxy-N-(1-isopropyl-2-methyl-4-pyrazolidinyl)benzamide dihydrochloride.

25. The method of claim 20 wherein the compound is 4-amino-5-chloro-2-methoxy-N-(1,2-diethyl-4-pyrazolidinyl)benzamide dihydrochloride.

* * * * *